United States Patent

Sumanaweera et al.

[11] Patent Number: 6,159,152
[45] Date of Patent: Dec. 12, 2000

[54] MEDICAL DIAGNOSTIC ULTRASOUND SYSTEM AND METHOD FOR MULTIPLE IMAGE REGISTRATION

[75] Inventors: Thilaka S. Sumanaweera, San Jose; Linyong Pang, Stanford; Said S. Bolorforosh, Palo Alto, all of Calif.

[73] Assignee: Acuson Corporation, Mountain View, Calif.

[21] Appl. No.: 09/196,987

[22] Filed: Nov. 20, 1998

Related U.S. Application Data

[60] Provisional application No. 60/105,705, Oct. 26, 1998.

[51] Int. Cl.[7] .................................................. A61B 8/00
[52] U.S. Cl. ................................................... 600/443
[58] Field of Search ................. 600/437, 443, 600/447, 454–456, 458; 382/128, 293–295; 128/916

[56] References Cited

U.S. PATENT DOCUMENTS

| | | | |
|---|---|---|---|
| 5,127,409 | 7/1992 | Daigle | 600/443 |
| 5,538,004 | 7/1996 | Bamber | 128/916 X |
| 5,575,286 | 11/1996 | Weng et al. | |
| 5,776,066 | 7/1998 | Nock et al. | 600/443 |
| 5,782,766 | 7/1998 | Weng et al. | 600/443 |
| 5,891,038 | 4/1999 | Seyed-Bolorforosh et al. | 600/447 |
| 5,946,425 | 8/1999 | Bove, Jr. et al. | 382/294 |
| 5,956,418 | 9/1999 | Aiger et al. | 382/154 |
| 5,999,662 | 12/1999 | Burt et al. | 382/284 |
| 6,014,473 | 1/2000 | Hossack et al. | 382/294 |
| 6,018,349 | 1/2000 | Szeliski et al. | 345/425 |

FOREIGN PATENT DOCUMENTS

WO 98/25509  11/1997  WIPO.

OTHER PUBLICATIONS

Linyong Pang, *Three–Dimensional Microscopy: Image Acquisition and Processing III*, 1996, SPIE vol. 2655, pp. 216–223.

*Primary Examiner*—Francis J. Jaworski
*Attorney, Agent, or Firm*—Craig A. Summerfield; Brinks Hofer Gilson & Lione

[57] ABSTRACT

A method and system for registration of multiple ultrasound images or frames of data are provided. The images are registered as a function of relative movement of the transducer. A feature or feature pattern, such as one or more structural edges, are identified in one image. The feature or feature pattern is represented by fewer than all of the data points within a frame of data. Based on the identification of a particular feature or feature pattern, relative motion is estimated by correlating the feature pattern with another image in various relative positions. The best correlation is selected. The motion is estimated by selecting a translation and rotation of the position associated with the best correlation. The frames of data are registered and compounded to generate the panoramic field of view image as a function of the estimated motion. The panoramic field of view image comprises a B-mode image, or a color Doppler image, or an image that is a combination of both. The imaging may be static or dynamic.

24 Claims, 2 Drawing Sheets

```
| | | | 0 -| -| -| -|
| | | | 0 -| -| -| -|
| | | | 0 -| -| -| -|
| | | | 0 -| -| -| -|
| | | | 0 -| -| -| -|
| | | | 0 -| -| -| -|
| | | | 0 -| -| -| -|
| | | | 0 -| -| -| -|
| | | | 0 -| -| -| -|
```

```
| | | | | | | | |
| | | | | | | | |
| | | | | | | | |
| | | | | | | | |
0 0 0 0 0 0 0 0 0
-| -| -| -| -| -| -| -| -|
-| -| -| -| -| -| -| -| -|
-| -| -| -| -| -| -| -| -|
-| -| -| -| -| -| -| -| -|
```

MEDICAL DIAGNOSTIC ULTRASOUND SYSTEM AND METHOD FOR MULTIPLE IMAGE REGISTRATION

REFERENCE TO EARLIER FILED APPLICATION

This application claims the benefit of the filing date pursuant to 35 U.S.C. §119(e) of Provisional Application Ser. No. 60/105,705, filed Oct. 26, 1998, the disclosure of which is hereby incorporated by reference.

BACKGROUND

This invention relates to a medical diagnostic ultrasound system and method for multiple image registration. In particular, frames of data associated with different azimuthal positions of a transducer are combined to form an panoramic field of view composite image. By registering data associated with the transducer array at various positions along the azimuthal axis, a larger compound image may be generated.

The data associated with the transducer array and the ultrasound system is collected in frames. Each frame of data represents one scan of a region. As a transducer is translated along the skin of a patient, other regions are scanned and a corresponding frame of data is stored. The region scanned for one frame of data may overlap with a region scanned for another frame of data. Therefore, each frame of data relates to another frame of data as a function of a translation in either or both of axial and azimuthal dimensions and a relative rotation.

Various algorithms for generating a panoramic field of view composite image are known. For example Weng et al., U.S. Pat. No. 5,575,286, disclose a method for estimating the translation and rotation between two or more images. A first image is divided into a plurality of subimage regions as a function of a block size. Using the arbitrarily selected sub-regions, speckle or other image data may be correlated to the second frame of data. A motion vector associated with translation in the azimuth and axial dimensions is estimated for each of the sub-regions. The relative position between the first image and a second image in terms of translation and rotation is estimated from the plurality of sub-region motion vectors.

The present invention is directed to a new system and method for registering a plurality of images as a function of relative translation and rotation.

BRIEF SUMMARY

The present invention is defined by the following claims, and nothing in this section should be taken as a limitation on those claims. By way of introduction, the preferred embodiment described below includes a method and system for registration of multiple ultrasound images or frames of data. The images are registered as a function of relative movement of the transducer. A feature or feature pattern, such as one or more structural edges, is identified in one image. The feature or feature pattern is represented by fewer than all of the data within a frame of data. Based on the identification of a particular feature or feature pattern, relative motion is estimated by correlating the feature pattern with another image in various relative positions. The best correlation is selected. The motion is estimated by selecting the translation and rotation for the relative position associated with the best correlation. The frames of data are registered and compounded to generate the panoramic field of view image as a function of the estimated motion.

Further aspects and advantages of the invention are discussed below in conjunction with the preferred embodiments.

DETAILED DESCRIPTION OF THE EMBODIMENTS

Figure 1:
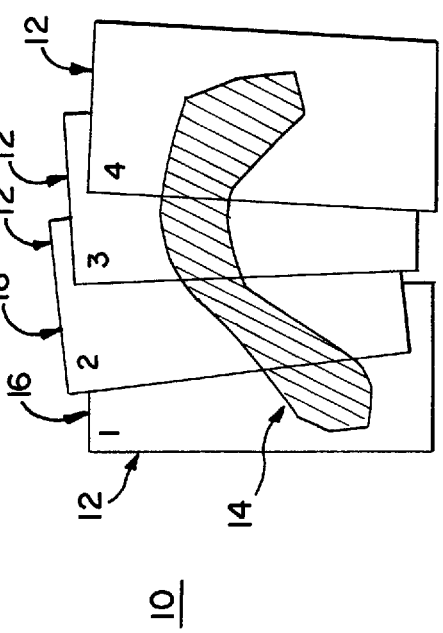
FIG. 1 is a representation of a composite image formed from four frames of data.

Referring to FIG. 1, a panoramic field of view composite image is shown at 10. The composite image 10 comprises four joined images 12. More or a fewer images 12 may be used. Within each of the images 12 is a structure or image feature 14. The structure or image feature 14 may comprise tissue borders or borders between tissue and added contrast agent. Preferably, at least a portion of the feature 14 in each image 12 is represented in at least one of the other adjacent images 12. Some images may not overlap or contain the feature 14.

To register one image 12, such as image 16, relative to another image 12, such as image 18, at least one portion of the feature 14 or another feature within the image 16 is identified. Preferably, the edge or other dominant aspect of the feature 14 is identified. The motion of one image relative to the other image is estimated by correlating the identified feature 14 in the first image 16 with the second image 18. As shown, the second image 18 is translated in the azimuth and axial dimensions and rotated relative to the first image 16. Other relative positions are possible. The estimated motion is used to generate the composite image 10.

Figure 2:
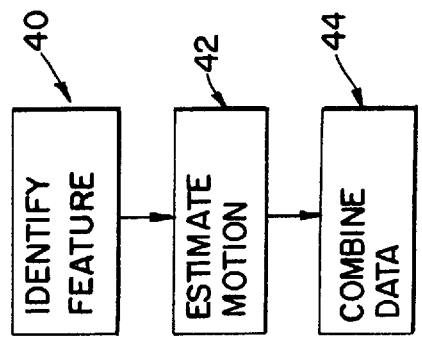
FIG. 2 is a block diagram of an ultrasound system for generating the composite image of FIG. 1.

Referring to FIG. 2, a block diagram of an ultrasound system for generating the composite image 10 is generally shown at 20. The ultrasound system 20 includes a transducer 22, a beamformer 24, a data processor 26, a scan converter 28, a display 30, and a control processor 32. The ultrasound system 20 may comprise an 128XP®, Aspen® or Sequoia® systems from Acuson Corporation. Other systems may be used, such as systems adapted to process ultrasound data (e.g. the Aegis® system from Acuson Corporation).

Based on control signals from the control processor 32, the beamformer 24 provides excitation signals to the transducer 22. The transducer 22 comprises one of a one-dimensional, two dimensional or 1.5D transducer. Various elements of the transducer 22 generate focused acoustical waveforms in response to the excitation signals. Based on the control instructions, a region of a patient is scanned in any of various formats, such as sector, Vector®, or linear. Other formats may be used. Echo signals responsive to the transmitted acoustic waveforms are received by the various elements of the transducer 22. In response, the transducer 22 generates echo signals. The beamformer 24 receives the echo signals and generates in-phase and quadrature data or other radio frequency (RF) data. The beamformer 24 may isolate information at a fundamental transmit frequency band or at a harmonic of the fundamental frequency.

The isolated in-phase and quadrature or RF data is provided to the data processor 26. The data processor 26 comprises a B-mode processor, a Doppler processor, or both the B-mode and the Doppler processor. The B-mode processor envelope detects the in-phase and quadrature data and log compresses the result to generate intensity data. The Doppler processor generates energy, velocity, or variance data or data representing combinations thereof from the in-phase and quadrature data.

Any of the data generated by the data processor 26 is scan converted by the scan converter 28 through interpolation or other processes. The scan converter 28 reformats the data from the polar coordinate pattern associated with the scan format to a Cartesian coordinate pattern for display. The scan converted data may be displayed on the display 30.

The control processor 32 controls the operation of various components of the ultrasound system 20. In one embodiment, the control processor 32 also processes ultrasound data for generation of a composite image. As used herein, ultrasound data includes data at intermediate stages within or data input or output from any one or more of the beamformer 24, the data processor 26, the scan converter 28 or the display 30. For example, the control processor has access to data output by the data processor 26 or data output by the scan converter 28. Preferably, the ultrasound data comprises B-mode intensity data prior to san conversion. In alternative embodiments, other ultrasound data is used for estimating motion. In one embodiment, frames of B-mode ultrasound data are used to estimate motion for the generation of a composite-panoramic field of view image of Doppler data, whether dynamic or static. Alternatively, Doppler ultrasound data is used for estimating the motion.

In alternative embodiments, the ultrasound data is transferred to a remote processor 34. The remote processor 34 comprises a personal computer, a workstation, a motion processor, or other processor for estimating motion. For example, the remote processor 34 comprises an AEGIS® system from Accuson Corporation. In yet other alternative embodiments, processors within any of the beamformer 24, data processor 26, scan converter 28 or display 30 estimate motion between two frames of ultrasound data.

A memory 36 is associated with the processor for estimating motion. The memory is 36 directly connected to the relevant processor or is remote from the processor. The memory 36 comprises a RAM device, VCR, solid state memory, disk drive or other memory device for storing frames of data.

Referring to FIGS. 1 and 2, the ultrasound system 20 generates frames of data corresponding to each image 12. As discussed above, each frame of data is in any of various formats, such as the linear format shown. Each image 12 is acquired sequentially in time as the transducer 22 is translated generally in the azimuthal direction. Assuming the transducer 22 is adjacent with the upper edge of each image 12 in FIG. 1, the azimuthal dimension corresponds to an X axis and the axial or range dimension corresponds to the Y axis (i.e. Z axis from the transducer 22). Each datum (i.e., pixel) in a frame of data represents a unique spatial location. For example, a frame of data includes a plurality of B-mode intensities. Each B-mode intensity is associated with an azimuthally positioned scan line and a range along the scan line. The position in the axial and azimuthal dimensions comprises location data.

The relative motion between any two frames of data is calculated as a function of the ultrasound data. Preferably, the relative motion between frames of data acquired sequentially without any intervening acquisitions is estimated. In alternative embodiments, one or more frames of data are acquired in between acquisition of the two frames of data used for determining relative motion. Triggering based on the cardiac cycle or other means for selecting frames of data associated with particular portion of the cardiac cycle may be used to select appropriate frames for combination, such as for creating a panoramic field of view image of Doppler data. The composite image 10 is generated as a function of the relative motion.

Figure 3:
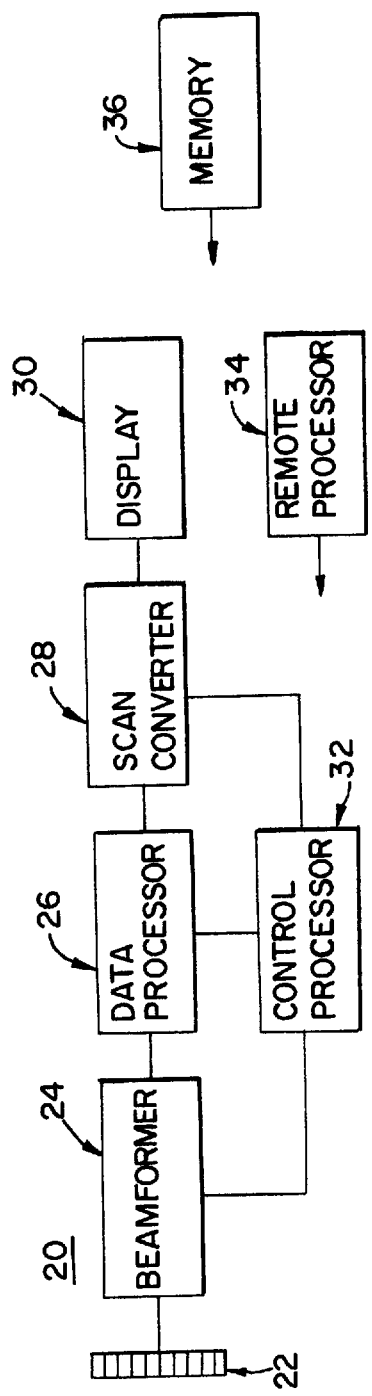
FIG. 3 is a flowchart for generating the panoramic field of view image shown in FIG. 1.

Referring to FIG. 3, a flow chart representing a method for generating the composite image 10 is shown. In step 40, a feature within a first frame of ultrasound data is identified. The motion between the first frame of ultrasound data and a second frame of ultrasound data is estimated in step 42. The first frame of data is acquired before or after the second frame of data. The first and second frames of ultrasound data are combined as a function of the estimated motion in step 44.

The feature identified in step 40 preferably includes an edge or other identifiable structure, such as associated with tissue, in the scanned region. The feature may comprise a plurality of features or a feature pattern.

The feature is preferably identified using one of various metrics, such as gradient, entropy or texture content. For example, artificial intelligence techniques using matched filters to correlate two frames of data based on a texture shape may be used. Preferably, gradient information is used to identify the feature. The location associated with a frame of data corresponding to the maximum gradient or change in ultrasound data amplitude is selected as the feature. For example, a location associated with an edge of an imaged structure is selected. If a plurality of equal gradient values exists, the first gradient value identified above a threshold or the first gradient value identified from all the maximum gradient values is selected as the feature. Other selection processes may be used, including selecting a plurality of locations associated with the maximum or other gradient values. Preferably, a substantially maximum gradient value is selected.

Figures 4A, 4B, 5:
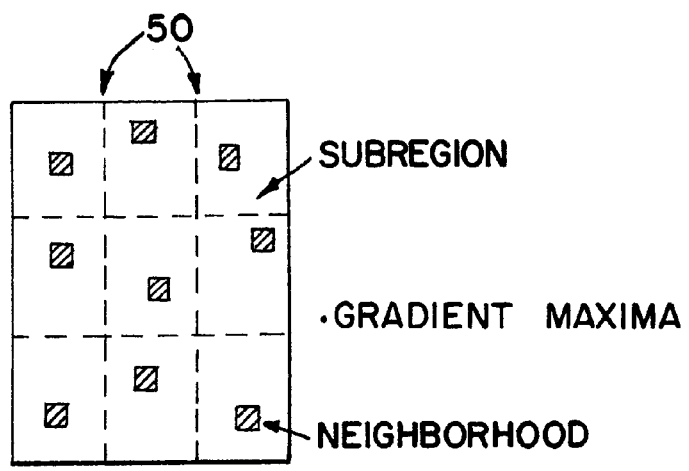
FIGS. 4A and 4B are representations of matrices of kernals.
FIG. 5 is a representation of a feature or feature pattern.

In one embodiment, the ultrasound data is convolved with one or more kernels or matrices to generate the gradient data. For example, azimuthal and axial gradient values are determined by using an azimuthal kernel and an axial kernel. In one embodiment, the azimuthal kernel comprises a nine by nine matrix as shown in FIG. 4A. The axial gradient is determined by convolving the ultrasound data with the kernel of FIG. 4B. In this embodiment, the kernels comprise nine by nine matrices. In alternative embodiments, the kernels comprise matrices of any size, such as 3 by 3 or 9 by 12. Furthermore, the kernel may be derived from a Gausian or Laplacian of a Gaussian or other functions. Other techniques to identify gradient or change information may be used, such as filters or look-up tables.

To convolve the X or azimuthal gradient, the kernel of FIG. 4A is aligned with the ultrasound datum of interest within the frame of data, such as aligning the upper left corner of the matrix with the datum. Using the neighboring ultrasound data and the datum of interest, an output gradient is determined by convolution with the kernel. The kernel is repositioned for the next datum of interest. The process is repeated until an X gradient is determined for all or a subset of all the locations represented by the ultrasound data. Likewise, the Y or axial gradient is determined.

For each location within the frame of data, the gradient magnitude is determined from the X and Y gradients. In one embodiment, the gradient magnitude is equal to the absolute value of the X gradient plus the absolute value of the Y gradient. In alternative embodiments, the true magnitude, the square root of the X gradient squared plus the Y gradient squared, is determined. Other gradient magnitude calculations may be used.

After the gradient magnitude is determined for each of all or a subset of all the locations within a frame of data, the gradient data is divided into sub-regions, such as shown in FIG. 5. The dashed lines 50 represent the division into sub-regions, such as the nine equal rectangular sub-regions shown. Other sub-regions may be used, including sub-regions of any shapes and patterns, whether or not equal in area. For example, the sub-regions are configured as hexagons, other polygons, circular sectors or as diagonals. Furthermore, the sub-regions may comprise a subset of the locations within the frame of data, such as selection of four corners represented by the frame of data. Division into sub-regions defines corresponding subsets of the frame of gradient or ultrasound data.

For each sub-region, one or more sub-features are identified as the locations associated with the maximum gradient value within the sub-region. The combined sub-features or maximum gradient within a plurality of sub-regions comprise a feature or a feature pattern within the frame of gradient or ultrasound data.

In one embodiment, the feature pattern is expanded to include locations adjacent or near the identified maximum gradient or sub-feature. The expansion identifies a neighborhood of locations. The neighborhood may include any grouping of locations, such as a five by five grouping of locations centered on the identified feature. Other neighborhood groupings, such as rectangular, circular or other shapes may be used. In one embodiment, the neighborhood includes a 10 by 10 region of locations with only every other location selected, effectively generating a five by five neighborhood expanded over a larger area. In alternative embodiments, the locations within a neighborhood are selected as a function of metric information, such as identifying locations adjacent the maximum gradient with gradient values above a threshold. Each neighborhood of locations corresponds to an identified sub-feature or feature, and the neighborhoods of the plurality of sub-regions corresponds to an identified feature pattern or feature.

The ultrasound data associated with the identified feature locations is selected. The selected ultrasound data is from the first frame of ultrasound data. The selected ultrasound data is correlated with ultrasound data in the second frame of ultrasound data. In alternative embodiments, the gradient data associated with the feature in the first frame is correlated with gradient data generated from the second frame of ultrasound data.

The motion between the two frames of ultrasound data is estimated by comparing the identified ultrasound data from the first frame of ultrasound data in different relative positions to the second frame of ultrasound data. Preferably, cross-correlation or a similar method is used for comparison. Such techniques (which will be referred to herein generally as correlation techniques) have been used for tracking blood flow. Preferably, a sum of absolute differences correlation technique is used.

For each of a plurality of comparisons, a correlation value is determined. The identified or selected information from the first frame of ultrasound data is translated and rotated to various positions to determine various correlation values. If a particular translation and rotation results in a sum of absolute differences that is close to zero, then it is probable that the first and second frames of ultrasound data have been aligned. The translation and rotation required to achieve the alignment indicates the motion between the two respective frames of ultrasound data. Identifying the lowest correlation value matches the images 12 with the movement of the transducer 22. In alternative embodiments, the maximum of a cross-correlation is selected as indicating the alignment for estimating motion.

Translation to different positions for determining correlation preferably corresponds to one or both of axial and azimuthal translation. In one embodiment, the selected ultrasound data and corresponding locations are translated in the azimuthal dimension by three locations on each side of an origin point and in the axial dimension by three locations from each side of the origin point. The selected ultrasound data is positioned relative to the second frame of ultrasound data at each possible integer location within the seven location range. Therefore, the selected locations and associated ultrasound data are translated to forty-nine different positions. The origin point is selected (1) as a location associated with no translation (2) as a location that is a function of a likely amount of translation or (3) as a location that is selected arbitrarily.

For each translation position, the selected ultrasound data is rotated by 0.1 degrees over a −2 to 2 degree range. Therefore, for each translation position, 41 rotational positions are provided. For each correlation value associated with a different rotation, ultrasound data is interpolated within the second frame of data to align with the rotated, selected ultrasound data and associated locations. In one embodiment, linear interpolation is used, but other interpolation methods may be provided. For each translational and rotational position, a correlation value of calculated. In this embodiment, 2,009 correlation values are determined. In other embodiments, different ranges and numbers of positions within the ranges for translations and rotations are used, such as determining correlation values for every other location position within a translation range with the same or an unequal number of locations on each side of the origin point.

In other alternative embodiments, past estimates of motion are used to determine the range of translations and rotations and the number of locations within a range on each side of the origin point. For example, if past estimates of motions show an average azimuthal translation of five pixels in one direction, the origin point is selected as a translation of five pixels in the direction of past motion. Additionally or alternatively, the previous estimates of motion are used to select a larger azimuthal translation range, such as twice the previous estimate of motion on one side of the original point. Furthermore, previous estimates of motion are used to identify an area for more dense determination of correlation values, such as determining a correlation value every second or third location position for locations representing motion that is opposite previous estimates.

In one embodiment, the origin point is selected as a function of initial translation in the azimuthal dimension only. The transducer is typically translated along the azimuthal dimension. Starting from a position associated with maximum overlap of the first frame of ultrasound data with the second frame of ultrasound data, the selected locations of the first frame of ultrasound data are translated over a range of 61 locations in the azimuthal direction, such as 30 locations in one direction and 30 locations in another direction in positional steps of one location each. Other ranges and positional steps may be used. A correlation value for each relevant location within the range is determined. In alternative embodiments, every other location or another function of the total number of locations within the range are used to determine correlation values. The position associated with the azimuthal location with the best alignment or correlation is selected as the origin point. The axial and azimuthal translation and rotation positioning as discussed above is then determined.

For the initial azimuthal translation or the final estimate of motion discussed above, a subset of the selected feature locations may be used. For example, the locations associated with a feature or feature pattern within a sub-region comprising half the azimuthal dimension locations and one-tenth of the axial dimension locations, centered adjacent the face of the transducer, are used. In one embodiment, the sub-set is used for the initial translation, and the entire feature or feature pattern is used for the subsequent azimuthal and axial translation and rotation for identifying the proper alignment to estimate motion.

After a correlation value is determined for each position associated with translation and rotation, the best alignment is selected. The amount of translation in the azimuthal and axial dimensions and the amount of rotation are determined as a function of the best alignment.

After estimating the motion, the first and second frames of ultrasound data are aligned as a function of the estimated motion. The two aligned frames of ultrasound data are superimposed. Preferably, the earlier acquired frame of ultrasound data is superimposed on the more recently acquired frame of ultrasound data. Typically, most of the older ultrasound data will almost exactly match the newer ultrasound data, but a small non-overlapping region will be present which represents ultrasound data acquired at the older image position which could not be acquired at the newer image position. Preferably, during the writing of the older data over the newer data, only the non-overlapping region is written. Other techniques for compounding the ultrasound data may be used, such as (1) using the data for the later-acquired frame of ultrasound data in any non-overlapping locations, (2) recursively averaging the later acquired frame of ultrasound data with the earlier acquired frame of ultrasound data for locations common to both, and (3) using weights to blend the first and second frame of ultrasound data in any overlapping areas. Estimation of motion and compounding are continued progressively for earlier frames of image data until all the frames in a sweep of the transducer 22 have been reassembled for display.

In one embodiment, a smooth interpolation scheme is used at the boundaries of overlapping and non-overlapping regions. Variable weighting factors starting with one for the first frame of ultrasound data and progressing down to zero are used to blend the frames of ultrasound data.

If the limits of the frame buffer for the display are exceeded during the panoramic field of view processing, the ultrasound data may be scaled to fit into the available frame buffer. Scaling may be achieved by remapping the ultrasound data to a new frame buffer using geometric transformation and interpolation, as is known in the computer graphics field.

In one embodiment, an error value or a value representing the confidence of the motion estimate is calculated using the correlation data. If the confidence value is low, a different estimate of motion is used, such as one derived from past or future estimates of motion.

The processing for generating a panoramic field of view composite image in two dimensions may be used for three dimensional imaging. Multiple sets of data associated with three dimensional locations are generated. A feature or feature pattern within one of the three-dimensional sets are identified and used to estimate motion between a first three-dimensional set and a second three-dimensional set of ultrasound data. The data of the two sets are combined as a function of the estimated motion.

While the invention has been described above by reference to various embodiments, it will be understood that many changes and modifications can be made without departing from the scope of the invention. For example, different methods of identifying a feature or feature pattern within an image may be used. Different methods for determining positions to calculate correlation values may be used. Ultrasound data associated with various processes, such as harmonic reception from tissue or contrast agent, may be used.

It is therefore intended that the foregoing details description be understood as an illustration of the presently preferred embodiments of the invention, and not as a definition of the invention. It is only the following claims, including all equivalents, that are intended to define the scope of the invention.

What is claimed is:

1. A method for combining at least two frames of ultrasound data with an ultrasound system, the method comprising the acts of:
   (a) selecting ultrasound data corresponding to at least one structure feature of a target in a first of the at least two frames of ultrasound data;
   (b) estimating motion between the first and a second of the at least two frames of ultrasound data as a function of the at least one structure feature; and
   (c) combining the first and second frames of ultrasound data as a function of the estimated motion.

2. The method of claim 1 wherein:
   act (a) comprises identifying a first group of location data as a function of the at least one structure feature, the first group of location data comprising a sub-set of locations associated with the first frame of ultrasound data; and
   act (b) comprises estimating the motion between the first and second frames of ultrasound data as a function of the first group of location data.

3. The method of claim 2 further comprising:
   (d) determining ultrasound data in the first frame of ultrasound data corresponding to the first group of location data; and
   wherein act (b) comprises estimating the motion between the first and second frames of ultrasound data as a function of the ultrasound data determined in act (d).

4. The method of claim 1 wherein act (a) comprises identifying a plurality of substantially maximum gradient locations represented by the first frame of ultrasound data.

5. The method of claim 4 further comprising:
   (d) convolving the first frame of ultrasound data;
   (e) determining a gradient magnitude as a function of the results of step (d); and
   wherein act (a) is responsive to act (e).

6. The method of claim 4:
   further comprising (d) separating the first frame of ultrasound data into a plurality of sub-sets of data representing sub-regions; and
   wherein each of the plurality of substantially maximum gradient locations is associated with a respective sub-region.

7. The method of claim 4 wherein act (a) further comprises, for each of the plurality of substantially maximum gradient locations, selecting a group of locations near the respective substantially maximum gradient location, the plurality of groups of locations comprising the at least one feature and at least a second structure feature; and wherein act (b) comprises estimating the motion as a function of the at least one and the at least the second structure features.

8. The method of claim 1 wherein act (b) comprises determining at least a first correlation value between data in the first frame of ultrasound data associated with the structure feature and the second frame of ultrasound data.

9. The method of claim 8 wherein act (b) further comprises determining a minimum sum of absolute differences.

10. The method of claim 8 where act (b) further comprises:

(b1) determining at least a second correlation value between data in the first frame of ultrasound data associated with the feature and the second frame of data, the second correlation value responsive to a different position of the data in the first frame of ultrasound data associated with the structure feature relative to the second frame of data, the different position selected from the group consisting of: rotation, azimuthal-axis translation, axial-axis translation and combinations thereof; and (b2) selecting a translation and a rotation as a function of the lowest of the at least first and second correlation values.

11. The method of claim 10 wherein the feature comprises a plurality of sub-features distributed in at least two sub-regions represented by the first frame of ultrasound data.

12. The method of claim 1 wherein act (a) comprises identifying the at least one structure feature as a function of a metric selected from the group consisting of: entropy and texture content.

13. The method of claim 1:

further comprising (d) separating the first frame of ultrasound data into a plurality of sub-sets of data representing sub-regions; and wherein the structure feature comprises a plurality of sub-features distributed in the respective plurality of sub-regions.

14. The method of claim 1 wherein act (b) comprises (b1) translating data in the first frame of ultrasound data associated with the structure feature to a first plurality of positions relative to the second frame of ultrasound data.

15. The method of claim 14 wherein act (b) further comprises (b2) rotating the data in the first frame of ultrasound data associated with the feature to a second plurality of positions relative to the second frame of ultrasound data.

16. The method of claim 15 wherein act (b) comprises estimating the motion as a function of correlation values for each position of the first and second plurality of positions.

17. The method of claim 15 wherein act (b) further comprises (b3):

(i) translating in an azimuthal dimension; and
(ii) determining a first correlation match as a function of azimuthal position;

wherein acts (b1) and (b2) are performed after determining the first correlation match; and wherein act (b) comprises estimating the motion as a function of a second correlation match.

18. The method of claim 1 wherein acts (a) and (b) comprise identifying and estimating as a function of B-mode data and further comprising step (d) of displaying a Doppler panoramic field of view image.

19. An ultrasound system for combining at least two frames of ultrasound data, the ultrasound system comprising:

a memory for storing the at least two frames of ultrasound data;

a processor for selecting ultrasound data corresponding to at least one structure feature of a target in a first of the at least two frames of ultrasound data and for estimating motion between the first and a second of the at least two frames of ultrasound data as a function of the at least one structure feature; and a scan converter for combining the first and second frames of ultrasound data as a function of the estimated motion.

20. The ultrasound system of claim 19 wherein the processor is operable to identify a plurality of substantially maximum gradient locations represented by the first frame of ultrasound data.

21. The ultrasound system of claim 19 wherein the structure feature comprises a feature pattern of a plurality of locations distributed in at least two sub-regions represented by the first frame of ultrasound data; and the processor is operable to determine at least two correlation values between data in the first frame of ultrasound data associated with the feature pattern and the second frame of ultrasound data as a function of rotation and translation of the data in the first frame of ultrasound data relative to the second frame of ultrasound data and to estimate the motion as a translation and a rotation as a function of the highest of the at least two correlation values.

22. A method for generating a panoramic field of view compound image, the method comprising the acts of:

(a) identifying a feature pattern in a first frame of ultrasound data;

(b) estimating motion between the first and a second frame of ultrasound data as a function of the feature pattern; and (c) combining the first and second frames of ultrasound data as a function of the estimated motion.

23. The method of claim 22 wherein act (a) comprises identifying a plurality of substantially maximum gradient locations represented by the first frame of data.

24. The method of claim 22 wherein:

act (a) comprises identifying the feature pattern wherein the feature pattern is distributed in at least two sub-regions represented by the first frame of data; and act (b) comprises:

(b1) determining at least two correlation values between data in the first frame of data associated with the feature pattern and the second frame of data as a function of rotation and translation of the data in the first frame of data relative to the second frame of data; and (b2) selecting a translation and a rotation as a function of the lowest of the at least two correlation values.

* * * * *